United States Patent [19]

Callejas

[11] 4,249,907
[45] Feb. 10, 1981

[54] TEMPERATURE CONTROL OF EXOTHERMIC REACTIONS

[75] Inventor: Ricardo J. Callejas, Maracaibo, Venezuela

[73] Assignee: Phillips Petroleum Company, Bartlesville, Okla.

[21] Appl. No.: 69,155

[22] Filed: Aug. 23, 1979

[51] Int. Cl.³ .............................................. C07B 1/00
[52] U.S. Cl. .................................. 23/230 A; 260/690; 260/698; 260/700; 364/500; 364/557; 422/62; 585/259; 585/263
[58] Field of Search ................... 422/62, 105, 108, 110; 23/230 A; 260/690, 698, 700; 585/259, 263; 364/500, 557

[56] References Cited

U.S. PATENT DOCUMENTS

| | | | |
|---|---|---|---|
| 3,471,582 | 10/1969 | Lupfer | 260/677 |
| 3,654,131 | 4/1972 | Carr | 208/57 |
| 3,656,911 | 4/1972 | Hobbs | 422/62 |

*Primary Examiner*—R. E. Serwin

[57] ABSTRACT

In a selective hydrogenation process wherein at least one catalyst bed is utilized, the temperature of the feed stream to the catalyst bed is controlled so as to maintain a desired reaction temperature in the catalyst bed. Primary control is based on an analysis of the feed stream. An override control based on the differential temperature across the at least one catalyst bed is provided to prevent fast changes in the composition of the feed stream from causing the temperature of the catalyst bed to change rapidly.

11 Claims, 1 Drawing Figure

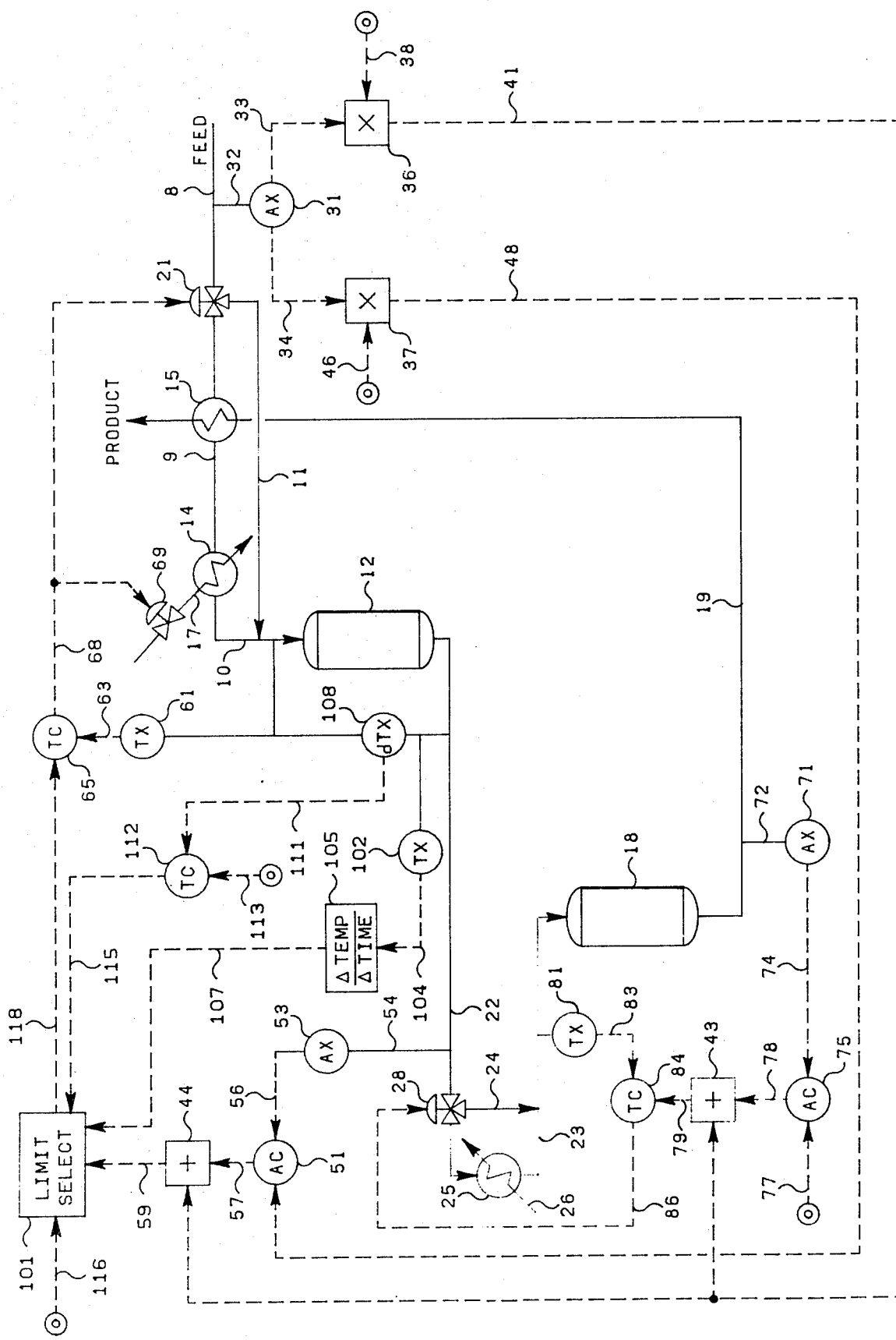

TEMPERATURE CONTROL OF EXOTHERMIC REACTIONS

This invention relates to temperature control of an exothermic reaction. In a specific aspect this invention relates to selective hydrogenation of unsaturated hydrocarbons in mixed hydrocarbon streams. In another specific aspect this invention relates to selective hydrogenation of acetylenic compounds in olefin-rich hydrocarbon streams.

In many exothermic chemical reactions it is necessary to control temperature within certain limits in order to maintain satisfactory yields and to prevent side reactions. This is particularly true in selective hydrogenation processes. For example, ethylene is commonly produced by the thermal cracking of hydrocarbon feedstocks. Unfortunately, some acetylene is also produced, and must be removed for many applications. This can be accomplished by selective catalytic hydrogenation of the acetylene.

In selective hydrogenation operations of this type, it is quite important to maintain the operating temperature within narrow limits. If the temperature is too low, the hydrogenation reaction is not carried out in a sufficiently complete manner to remove the acetylene. If the temperature becomes too high, side reactions such as the hydrogenation of ethylene and the formation of polymers may result. It is also very important to prevent excessive temperatures from being reached because of the danger of explosions.

In the past it has been common to control selective hydrogenation processes based on an analysis of the feed stream supplied to the selective hydrogenation process. For example, in the selective catalytic hydrogenation of acetylene, an analysis of the acetylene concentration in the feed stream and an analysis of the carbon monoxide concentration in the feed stream is utilized to control the temperature of the catalyst bed. A fluctuation in either the concentration of the acetylene or the concentration of carbon monoxide in the feed stream will typically require a change in the catalyst bed temperature to maintain the concentration of acetylene in the effluent flowing from the catalyst bed under a desired level.

It has been found that temperature control based on the analysis of the feed stream may allow the temperature of the catalyst bed to increase very rapidly under certain operating conditions. Specifically, if the concentration of the component in the feed stream which is being utilized to control the temperature of the catalyst bed changes rapidly, the analyzer may not be able to react quickly enough to prevent a rapid increase of the temperature in the catalyst bed. This runaway condition may result in dangerous temperatures being reached and may also result in excessive hydrogenation of a desired product such as ethylene.

It is thus an object of this invention to provide method and apparatus for controlling the reaction temperature of an exothermic chemical reaction process. Another object of this invention is to provide method and apparatus for controlling the selective hydrogenation of unsaturated hydrocarbons in mixed hydrocarbon streams. Still another object of this invention is to provide method and apparatus for controlling the selective hydrogenation of acetylenic compounds in olefin-rich hydrocarbon streams. Still another object of this invention is to provide protective override control for the exothermic chemical reaction process where the primary control of the reaction temperature of the exothermic chemcial reaction process is based on an analysis of the feed flowing to the exothermic chemical reaction process.

In accordance with the present invention, a selective hydrogenation process which utilizes a catalyst bed or reaction zone is controlled so as to maintain a desired reaction temperature in the catalyst bed. The feed stream to the reactor is split into at least two portions. A first portion of the feed stream to the reactor is heated before being passed to the reactor. A second portion of the feed stream to the reactor is utilized as a quench fluid and is introduced into the first portion of the feed stream to the reactor after the first portion of the feed stream to the reactor has been heated.

An analysis of the feed stream flowing to the reactor is utilized to provide an indication of the amount of acetylene in the feed stream and also an indication of the amount of carbon monoxide in the feed stream. An analysis of the effluent flowing from the reactor is utilized to provide an indication of the amount of acetylene in the effluent flowing from the reactor. Based on the analysis of the amount of acetylene in the feed stream flowing to the reactor and the analysis of the amount of acetylene in the effluent flowing from the reactor, the temperature of the feed stream flowing to the reactor is controlled by manipulating the amount of heat supplied to the feed stream and/or by manipulating the amount of feed stream which is diverted as quench fluid so as to maintain a desired reaction temperature in the first reactor. The analysis of the amount of carbon monoxide in the feed stream flowing to the reactor is utilized to bias the temperature control of the feed stream flowing to the first reactor.

An override control system is provided to override the temperature control based on the analysis of the feed stream flowing to the reactor where the concentration of the acetylene or carbon monoxide changes rapidly. The temperature differential across the reactor is compared to the desired temperature differential across the reactor to establish a control signal which may be utilized to manipulate the temperature of the feed stream flowing to the reactor under certain conditions. The rate of change of the temperature of the effluent flowing from the reactor is monitored and compared to a limit on the rate of change. If the rate of change of the temperature of the effluent flowing from the reactor is greater than the limit set point then the control signal which is based on the temperature differential across the reactor is utilized to control the temperature of the feed flowing to the reactor. Control is returned to the control signal based on the analysis of the feed stream flowing to the reactor when the rate of change of the temperature of the effluent flowing from the reactor falls back below the limit set point.

In this manner, the required reaction temperature is maintained in the reactor even under conditions of rapid changes in the concentration of acetylene and/or carbon monoxide in the feed stream flowing to the reactor.

Other objects and advantages of the invention will be apparent from the foregoing brief description of the invention and from the appended claims as well as from the detailed description of the drawing in which:

FIG. 1 is a schematic diagram of a selective hydrogenation process with an associated control system.

The invention is illustrated and described in terms of a selective hydrogenation process for the hydrogenation of acetylene in an ethylene product. However, it should be understood that this invention can be utilized for carrying out other selective hydrogenation processes such as the conversion of diolenfins to olefinic and/or saturated compounds. The invention is also applicable to other processes, other than selective hydrogenation processes, for removing a constituent from a feed stream.

The invention is also described in terms of a selective hydrogenation process in which two reactors in series are utilized. This particular reactor configuration is preferred for the selective hydrogenation of acetylene in an ethylene product. However, the invention is applicable to use of only a single reactor or more than two reactors. Also the invention is described in terms of override control on only the temperature of the first reactor in the series of two reactors. The invention is, however, applicable to override control of both of the reactors or only the second reactor in the series. However, it is presently preferred to apply the override control to only the temperature control of the first reactor in the series.

Although the invention is illustrated and described in terms of a specific hydrogenation process, the applicability of the invention described herein extends to other process configurations such as using different reactor configurations or using different heat exchanger configurations. The invention also extends to different types of control system configurations which accomplish the purpose of the invention. Lines designated as signal lines in the drawings are pneumatic in this preferred embodiment. However, this invention is also applicable to electrical, mechanical, hydraulic or other signal means for transmitting information. In many control systems some combination of these types of signals will be used. However, use of any other type of signal transmission, compatible with the process and equipment in use, is within the scope of the invention.

The controllers shown may utilize the various modes of control such as proportional, proportional-integral, proportional-derivative or proportional-integral-derivative. In this preferred embodiment proportional-integral controllers are utilized but any controller capable of accepting two input signals and producing a scaled output signal, representative of a comparison of the two input signals, is within the scope of the invention. The operation of proportional-integral controllers is well known in the art. The output control signal of a proportional-integral controller may be represented as $$S = K_1 E + K_2 \int E dt$$

where

S = output control signal;
E = difference beetween two input signals; and
$K_1$ and $K_2$ = constants.

The scaling of an input signal by a controller is well known in control system art. Essentially, the output of a controller may be scaled to represent any desired factor or variable. An example of this is where a desired temperature and an actual temperature is compared by a controller. The output could be a signal representative of a desired change in the flow rate of some fluid necessary to make the desired and actual temperatures equal. On the other hand, the same output signal could be scaled to represent a percentage or could be scaled to represent a pressure change required to make the desired and actual temperatures equal. If the controller output can range from 3 to 15 lbs., which is typical, then the output signal could be scaled so that an output signal having a pressure of 9 lbs. corresponds to 50 percent, some specified flow rate, or some specified pressure.

The various transducing means used to measure parameters which characterize the process and the various signals generated thereby may take a variety of forms or formats. For example, the control elements of the system can be implemented using electrical analog, digital electronic, pneumatic, hydraulic, mechanical or other types of equipment or combinations of one or more of such equipment types. While the presently preferred embodiment of the invention preferably utilizes pneumatic control elements in conjunction with pneumatic and electrical signal handling and translation apparatus, the apparatus and method of the invention can be implemented using a variety of specific equipment available to and understood by those skilled in the process control art. Likewise, the format of the various signals can be modified substantially in order to accommodate signal format requirements of a particular installation, safety factors, the physical characteristics of the measuring or control instruments and other similar factors. For example, a measurement of a system parameter may exhibit a generally proportional relationship to the square of the actual system parameter. Other measuring instruments might produce a signal which is proportional to the measured parameter, and still other measuring instruments may produce a signal which bears a more complicated, but known, relationship to the measured system parameter. In addition all signals could be translated into a "suppressed zero" or other similar format in order to provide a "live zero" and prevent an equipment failure from being erroneously interpreted as a low (or high) measurement or control signal. Regardless of the signal format or the exact relationship of the signal format or the exact relationship of the signal to the parameter which it represents, each signal representative of a measured process parameter or representative of a desired process value will bear a relationship to the measure parameter or desired value which permits designation of a specific measured or desired value by a specific signal value. A signal, which is representative of a process measurement or desired process value, is therefore one from which the information regarding the measured or desired value can be readily retrieved regardless of the exact mathematical relationship between the signal units and the measured or desired process units.

Referring now to the drawing, an ethylene feed stream containing some concentration of acetylene and carbon monoxide is introduced through conduit means 8, 9 and 10 to the reactor 12 which contains a first catalyst bed containing a hydrogenation catalyst. Heat exchanger 14 is operably located between conduit means 9 and 10. Steam or another suitable heating fluid is provided through conduit means 17 to the heat exchanger 14 and is utilized to provide heat to the feed flowing through conduit means 8, 9 and 10. Heat exchanger 15 is operably located between conduit means 8 and 9. The product stream from the reactor 18, which flows through conduit means 19, is provided to the heat exchanger 15 and is also utilized to provide heat to the feed stream flowing through conduit means 8, 9 and 10. The pneumatic control valve 21 is operably located in conduit means 8 and is utilized to split the flow of the feed between conduit means 8 and the bypass conduit means 11. The feed flowing through conduit means 10 and the bypass conduit means 11 are preferably mixed before the feed enters the reactor 12. The feed flowing through the bypass conduit means 11 is utilized as a quench fluid to provide further temperature control of the feed flowing to the reactor 12.

The effluent flowing from the reactor 12 is passed through conduit means 22 and 23 to the reactor 18 which contains a second catalyst bed containing the hydrogenation catalyst. Heat exchanger 25 which is operably located between conduit means 22 and 23 is utilized to provide a means for cooling the effluent flowing through conduit means 22 and 23. A cooling fluid such as water is provided through conduit means 26 to the heat exchanger 25. The pneumatic control valve 28, which is operably located in conduit means 22, is utilized to control the relationship between the amount of effluent flowing from the reactor 12 which flows to the reactor 18 through the heat exchanger 25 and through the bypass conduit means 24. The effluent flowing through conduit means 24 may be considered the primary effluent stream and the effluent flowing through conduit means 22, the heat exchanger means 25, and conduit means 23 may be considered the quench fluid stream. The two fluid streams flowing through conduit means 24 and conduit means 23 are preferably mixed before entering the reactor 18.

The ethylene product, which have a very low concentration of acetylene, is removed from the reactor 18 through conduit means 19. As has been previously stated the product removed through conduit means 19 from the reactor 18 flows through the heat exchanger 15 to provide heat to the feed flowing through conduit means 8, 9 and 10 to the reactor 12.

A sample of the feed flowing through conduit means 8 is passed through conduit means 32 to analyzer transducer 31, which is preferably a chromatographic analyzer. Analyzer transducer 31 provides two output signals in response to the analysis of the feed flowing through conduit means 8. Signal 33 is representative of the concentration of the carbon monoxide in the feed flowing through conduit means 8. Signal 34, from the analyzer transducer 31 is representative of the concentration of the acetylene in the feed through conduit means 8. Signal 33 is provided from the analyzer transducer 31 to the multiplying means 36. Signal 34 is provided from the analyzer transducer 31 to the multiplying means 37.

Carbon monoxide tends to poison the hydrogenation catalyst. If the concentration of carbon monoxide in the feed flowing to conduit means 8 changes, the temperature required for the hydrogenation of acetylene in the reactors 12 and 18 also changes. The multiplying means 36 is supplied with a set point signal 38 which is representative of the change in the temperature which is required for a given degree of change in the concentration of carbon monoxide in the feed flowing to conduit means 8. In the preferred embodiment of this invention the set point signal 38 is equal to 1° F/0.01 percent CO. Thus, if the concentration of carbon monoxide is 0.1 mol percent in the feed flowing through conduit means 8, the output signal 41 from the multiplying means 36 will be representative of 10° F. The output signal 41 from the multiplying means 36 provides a means for compensating for the concentration of carbon monoxide in the feed flowing through conduit means 8 by raising the temperature of the hydrogenation reaction in reactors 12 and 18 to compensate for the carbon monoxide concentration in the feed flowing through conduit means 8. It is noted that the concentration of carbon monoxide in the feed flowing through conduit means 8 will be essentially equal to the concentration of carbon monoxide flowing through the conduit means 22 from the reactor 12. Signal 41 from the multiplying means 36 is provided as a first input to the summing means 43 and to the summing means 44.

The multiplying means 37 is provided with a set point signal 46 which is representative of the desired relationship between the percentage of the total conversion of acetylene which is accomplished in reactor 12 and the percentage of the total conversion of acetylene which is accomplished in reactor 18. Thus, if it is desired that 75 percent of the conversion of the acetylene takes place in reactor 12 and 25 percent of the required conversion of acetylene takes place in reactor 18, signal 46 is representative of 25 percent. Preferably 70 to 80 percent of the acetylene is converted in reactor 12 with 20 to 30 percent of the acetylene being converted in reactor 18. Signal 34, which is representative of the concentration of acetylene in the feed flowing through conduit means 8, is multiplied by signal 46 to produce signal 48 which is output from the multiplying means 37. Signal 48 is equal to the desired concentration of acetylene in the effluent flowing from the reactor means 12 through conduit means 22. Signal 48 is provided as a first input to the analyzer controller 51.

A sample of the feed stream flowing through conduit means 22 is passed through conduit means 54 to the analyzer transducer 53, which is preferably a chromatographic analyzer. Analyzer transducer 53 provides an output signal 56 which is representative of the measured concentration of the acetylene in the effluent flowing through conduit means 22. Signal 56 is provided from the analyzer transducer 53 as a second input to the analyzer controller 51. The analyzer controller 51 compares signal 56 with signal 48. In response to this comparison the analyzer controller 51 provides an output signal 57 which is representative of the temperature change required to make the concentration of the acetylene in the effluent flowing through conduit means 22 equal to the desired concentration represented by signal 48. Signal 57 is supplied from the analyzer controller 51 as a second input to the summing means 44. In response to signal 41, the summing means 44 provides an output signal 59 which is representative of the desired temperature of the feed flowing through conduit means 10 into the reactor 12 based on the analysis control. Signal 59 is supplied as a first input to the limit select 101.

Temperature transducer 102, in combination with a temperature mesuring device such as a thermocouple which is operably located in conduit means 22, provides an output signal 104 representative of the temperature of the effluent flowing through conduit means 22. Signal 104 is provided from the temperature transducer 102 to the $\Delta$temp/$\Delta$time block 105. Signal 104 is utilized to establish signal 107 which is representative of the rate of change of the temperature of the effluent flowing through conduit means 22. Signal 107 is provided from the $\Delta$temp/$\Delta$time block 105 as a second input to the limit select 101.

The differential temperature transducer 108, in conjunction with temperature measuring devices such as thermocouples which are operably located in conduit means 10 and 22, provides an output signal 111 which is representative of the temperature differential across the reactor 12. Signal 111 is provided from the differential temperature transducer 108 as an input to the temperature controller 112. The temperature controller 112 is also provided with a set point signal 113 which is representative of the desired temperature differential across the reactor 12. In response to signals 111 and 113, the temperature controller 112 provides an output signal 115 which is responsive to the difference between signals 111 and 113. Signal 115 is provided from the temperature controller 112 as a third input to the limit select 101.

The limit select 101 is also provided with a set point signal 116 which will be referred to as the limit set point. In response to the described inputs, the limit select 101 provides an output signal 118 which is representative of the desired temperature of the feed flowing through conduit means 10 into the reactor 12. Signal 118 is provided from the limit select 101 as an input to the temperature controller 65.

The logic for the limit select 101 is as follows:

if $\left|\frac{\Delta temp}{\Delta time}\right| \leq$ limit set point    select signal 59 if $\left|\frac{\Delta temp}{\Delta time}\right| >$ limit set point    select signal 115

The limit set point 116 is essentially a limitation on the rate of change of the temperature of the effluent flowing through conduit means 22. If the rate of change represented by signal 107 is less than the limit set point, then the primary control system based on the analysis of the feed flowing to the reactor 12 is utilized to control the temperature of the feed flowing through conduit means 10 to the reactor 12. If the rate of change of the temperature of the effluent flowing through conduit means 22 is greater than the limit set point, then signal 115 is selected and signal 118 will be substantially equal to the signal 115. Control of the temperature of the effluent flowing to the reactor 12 through conduit means 10 will then be based upon the temperature differential across the reactor 12.

If rapid changes occur in the concentration of either acetylene or carbon monoxide in the feed flowing to the reactor 12, the cycle time of the analyzer transducer 31 may be such that the control based upon the analysis of the feed cannot react quickly enough to prevent large temperature increases in the reactor 12. However, changes in the concentration of either acetylene or carbon monoxide in the feed flowing to reactor 12 almost immediately cause a change in the temperature of the effluent flowing through conduit means 22. Thus, the reactor 12 may be thought of as providing a very fast, rough analysis of any changes in the concentration of either acetylene or carbon monoxide in the feed flowing to reactor 12. Thus, the temperature differential across reactor 12 may be utilized for secondary or override control of the temperature of the feed stream flowing through conduit means 10 to the reactor 12. The override control will be in effect only when rapid changes occur in the concentration of the acetylene or carbon monoxide in the feed stream flowing to the reactor 12. The override control system will act to prevent a runaway of the temperature of the reactor 12 until such time as the control system based on the analysis of the feed stream has had time to react to the rapid changes in the concentration of either acetylene and/or carbon monoxide. Thus, signal 118 will typically be equal to signal 59 unless rapid changes occur in the concentration of acetylene or carbon monoxide in the feed flowing to the reactor 12. If rapid changes occur which cannot be controlled by the control system based on the analysis of the feed stream then signal 118 will typically be equal to signal 115 to prevent temperature runaways in the reactor 12.

The set point 113 to the temperature controller will typically range from about 10° to about 40° F. with 20° F. being preferred. The limit set point 116 will typically have a range of about 5° to about 50° F./minute with 10° F./minute being preferred.

Temperature transducer 61 together with a temperature measuring instrument such as a thermocouple, which is located in conduit means 10, provides an output signal 63 which is representative of the measured temperature of the feed flowing through conduit means 10 into the reactor 12. This measurement is preferably obtained after the quench fluid flowing through conduit means 11 has been mixed with the feed flowing through conduit means 10. Signal 63 is provided as a second input to the temperature controller 65. The temperature controller 65 compares signal 63 and signal 118 to provide an output signal 68 which is responsive to the difference between signals 63 and 118. Signal 68 is provided to the pneumatic control valve 69 which is operably located in conduit means 17 and is provided to the pneumatic control valve 21. Pneumatic control valves 69 and 21 are manipulated in response to signal 68 to thereby control the temperature of the feed flowing through conduit means 10 into the reactor 12.

Split range control is utilized to control the temperature of the feed flowing through conduit means 11 into the reactor 12. Pneumatic control valve 69 is fully open when signal 68 from the temperature controller 65 has a value less than or equal to 3 pounds. Pneumatic control valve 69 is fully closed when signal 68 has a value greater than or equal to 9 pounds. Pneumatic control valve 21 allows no feed to flow through conduit means 11 when the signal 68 is less than or equal to 9 pounds. Pneumatic control valve 21 diverts all of the feed flowing through conduit means 8 to conduit means 11 when signal 68 is greater than or equal to 15 pounds. Thus the feed flowing through conduit means 10 into the reactor 12 will have a maximum temperature when signal 68 has a value of 3 pounds or less and will have a minimum temperature when signal 68 has a value of 15 pounds or greater.

It is noted that this control of both the flow rate of the heating fluid through conduit means 17 and the split of the feed stream is preferable. However, either could be used as a stand alone control, if desired, to manipulate the temperature of the feed stream flowing through conduit means 10 to the reactor 12. Control of both provides a more responsive temperature control.

A sample of the effluent stream flowing through conduit means 19 is passed through conduit means 72 to the analyzer transducer 71 which is preferably a chromatographic analyzer. Analyzer transducer 71 provides an output signal 74 which is representative of the acetylene concentration in the product stream flowing through conduit means 19. Signal 74 is provided from the analyzer transducer 71 as a first input to the analyzer controller 75. The analyzer controller 75 is also provided with a set point signal 77 which is representative of the desired acetylene concentration in the product flowing through conduit means 19. The analyzer controller 75 compares signal 74 with signal 77 to provide an output signal 78 which is representative of any change in the temperature of the feed flowing through conduit means 23 into reactor 18 required to maintain the acetylene concentration in the product flowing through conduit means 19 equal to the desired acetylene concentration represented by signal 77. Signal 78 is provided from the analyzer controller 75 as a second input to the summing means 43. In response to signal 78 and signal 41, the summing means 43 provides an output signal 79 which is representative of the desired temperature of the feed flowing through conduit means 23 into the reactor 18.

Temperature transducer 81 together with a temperature measuring element such as a thermocouple, which is operably located in conduit means 23, provides an output signal 83 which is representative of the measured temperature of the effluent flowing through conduit means 23 into the reactor 18. Signal 83 is provided from the temperature transducer 81 as a second input to the temperature controller 84. In response to the comparison of signal 83 and signal 79, the temperature controller 84 provides an output signal 86 to the pneumatic control valve 28. The pneumatic control valve 28 is manipulated in response to signal 86 to provide sufficient effluent from the reactor 12 to the cooling heat exchanger 25 to maintain the desired temperature of the effluent flowing through conduit means 23 into the reactor 18. In this preferred embodiment when signal 86 has a value equal to or less than 3 pounds, the pneumatic control valve 28 operates to completely bypass the cooling heat exchanger 25. When the control signal 86 has a value greater than or equal to 15 pounds the pneumatic control valve 28 operates to direct all of the effluent flowing from the reactor 12 to the reactor 18 through the cooling heat exchanger 25.

The invention has been described in terms of a control system for a selective hydrogenation process in which two catalyst beds are utilized. Independent control systems for each reactor or catalyst bed have been described with differential temperature override control of the present invention being preferably applied only to the first reactor. It is again noted that the invention is applicable to only a single reactor or more than two reactors and the differential temperature override control could be applied to both of the reactors or only the second reactor if desired.

The invention has been described in terms of a presently preferred embodiment as is illustrated in FIG. 1. Specific components which can be used in the practice of the invention as illustrated in FIG. 1 such as pneumatic control valves 21, 28 and 69; differential temperature transducer 108; temperature transducers 61, 81 and 102; temperature controllers 51, 75, 65, 84 and 112; multiplying means 36 and 37; and summing means 43 and 44 are each well known, commercially available control components such as are described at length in Perry's Chemical Engineers' Handbook, 4th Edition, Chapter 22, McGraw-Hill.

Analyzer transducers 31, 53 and 71 are preferably chromatographic analyzers such as the Model 102 Process Chromatograph System, manufactured by Applied Automation Inc., Bartlesville, Okla. The limit select 101 and the Δtemp/Δtime block 105 may be implemented on either an analog or digital computer. Preferably the Optrol 3600 digital control computer manufactured by Applied Automation, Inc. is utilized to implement the limit select 101 and the Δtemp/Δtime block 105.

For reasons of brevity, conventional auxillary equipment such as pumps, additional heat exchangers, additional measurement-control devices, etc. have not been included in the above description as they play no part in the explanation of the invention.

While the invention has been described in terms of the presently preferred embodiment, reasonable variations and modifications are possible by those skilled in the art, within the scope of the described invention and the appended claims. Variations such as utilizing the control system of the present invention in different selective hydrogenation processes or using more than two reactors is within the scope of the invention.

That which is claimed is:

1. Apparatus comprising:
   a catalyst bed;
   means for supplying a feed stream containing a first constituent to said catalyst bed, at least a portion of said first constituent in said feed stream being removed from said feed stream in said catalyst bed;
   means for withdrawing the reaction effluent, containing a substantially reduced concentration of said first constituent, from said catalyst bed;
   means for establishing a first signal representative of the concentration of said first constituent in said feed stream;
   means, responsive to said first signal, for establishing a second signal representative of the temperature of said feed stream necessary to maintain the desired concentration of said first constituent in said reaction effluent;
   means for establishing a third signal representative of the difference between the temperature of said reaction effluent and the temperature of said feed stream;
   means, responsive to said third signal, for establishing a fourth signal representative of the temperature of said feed stream necessary to maintain a desired difference between the temperature of said reaction effluent and the temperature of said feed stream;
   means for establishing a fifth signal representative of the rate of change of the temperature of said reaction effluent;
   means for establishing a sixth signal representative of a limit on the rate of change of the temperature of said reaction effluent; and
   means for manipulating the temperature of said feed stream in response to said second signal if the magnitude of said fifth signal is less than or equal to the magnitude of said sixth signal and for manipulating the temperature of said feed stream in response to said fourth signal if the magnitude of said fifth signal is greater than the magnitude of said sixth signal.

2. Apparatus in accordance with claim 1 wherein said means for establishing said second signal comprises:
   means, responsive to said first signal, for establishing a seventh signal representative of the desired concentration of said first constituent in said reaction effluent;
   means for establishing an eighth signal representative of the actual concentration of said first constituent in said reaction effluent; and
   means for comparing said seventh signal and said eighth signal and for establishing said second signal responsive to the difference between said seventh signal and said eighth signal.

3. Apparatus in accordance with claim 1 wherein said means for establishing said fourth signal comprises:

means for establishing a seventh signal representative of the desired difference between the temperature of said reaction effluent and the temperature of said feed stream; and means for comparing said third signal and said seventh signal and for establishing said fourth signal responsive to the difference between said third signal and said seventh signal.

4. Apparatus in accordance with claim 1 wherein said means for establishing said fifth signal comprises:

means for establishing a seventh signal representative of the temperature ($TEMP_1$) of said reaction effluent at a time of $t_1$;

means for establishing an eighth signal representative of the temperature ($TEMP_2$) at a time $t_2$, said time $t_2$ being later in time than said time $t_1$;

means for subtracting said seventh signal from said eighth signal to establish a ninth signal representative of $TEMP_2-TEMP_1$;

means for establishing a tenth signal representative of $t_2-t_1$; and means for dividing said ninth signal by said tenth signal to establish said fifth signal.

5. Apparatus in accordance with claim 1 wherein said means for manipulating the temperature of said feed stream in response to said second signal if the magnitude of said fifth signal is less than or equal to the magnitude of said sixth signal and for manipulating the temperature of said feed stream in response to said fourth signal if the magnitude of said fifth signal is greater than the magnitude of said sixth signal comprises:

means for establishing a seventh signal representative of the actual temperature of said feed stream;

means for comparing said seventh signal to said second signal or said fourth signal and for establishing an eighth signal responsive to the difference between said seventh signal and said second signal or said fourth signal; and means for manipulating the temperature of said feed stream in response to said eighth signal.

6. A method for providing control of the primary control of the temperature of a selective hydrogenation process in which at least a portion of a first constituent in a feed stream is removed from said feed stream in a catalyst bed comprising the steps of:

establishing a first signal representative of the difference between the temperature of the reaction effluent flowing from said catalyst bed and the temperature of said feed stream;

responsive to said first signal, establishing a second signal representative of the temperature of said feed stream necessary to maintain a desired difference between the temperature of said reaction effluent and the temperature of said feed stream;

establishing a third signal representative of the rate of change of the temperature of said reaction effluent;

establishing a fourth signal representative of a limit on the rate of change of the temperature of said reaction effluent; and overriding the primary control of said selective hydrogenation process to thereby manipulate the temperature of said feed stream in response to said second signal if the magnitude of said third signal is greater than the magnitude of said fourth signal.

7. A method in accordance with claim 6 wherein said primary control comprises:

establishing a fifth signal representative of the concentration of said first constituent in said feed stream;

responsive to said fifth signal, establishing a sixth signal representative of the temperature of said feed stream necessary to maintain the desired concentration of said first constituent in said reaction effluent; and manipulating the temperature of said feed stream in response to said sixth signal.

8. A method in accordance with claim 7 wherein said step of establishing said sixth signal comprises:

responsive to said fifth signal, establishing a seventh signal representative of the desired concentration of said first constituent in said reaction effluent;

establishing an eighth signal representative of the actual concentration of said first constituent in said reaction effluent; and comparing said seventh signal and said eighth signal and establishing said sixth signal responsive to the difference between said seventh signal and said eighth signal.

9. A method in accordance with claim 6 wherein said step of establishing said second signal comprises:

establishing a fifth signal representative of the desired difference between the temperature of said reaction effluent and the temperature of said feed stream; and comparing said first signal and said fifth signal and establishing said second signal responsive to the difference between said first signal and said fifth signal.

10. A method in accordance with claim 6 wherein said step of establishing said third signal comprises:

establishing a fifth signal representative of the temperature ($TEMP_1$) of said reaction effluent at a time $t_1$;

establishing a sixth signal representative of the temperature ($TEMP_2$) at a time $t_2$, said time $t_2$ being later in time than said time $t_1$;

subtracting said fifth signal from said sixth signal to establish a seventh signal representative of $TEMP_2-TEMP_1$;

establishing an eighth signal representative of $t_2-t_1$; and dividing said seventh signal by said eighth signal to establish said third signal.

11. A method in accordance with claim 6 wherein said step of manipulating the temperature of said feed stream in response to said second signal comprises:

establishing a fifth signal representative of the actual temperature of said feed stream;

comparing said fifth signal and said second signal and establishing a sixth signal responsive to the difference between said second signal and said fifth signal; and manipulating the temperature of said feed stream in response to said sixth signal.

* * * * *

UNITED STATES PATENT AND TRADEMARK OFFICE
CERTIFICATE OF CORRECTION

PATENT NO. : 4,249,907
DATED : February 10, 1981
INVENTOR(S) : Ricardo J. Callejas It is certified that error appears in the above–identified patent and that said Letters Patent are hereby corrected as shown below:

Column 11, claim 6, line 42, after "providing" insert --- override ---

Signed and Sealed this

Twenty-eighth Day of July 1981

[SEAL]

*Attest:*

*Attesting Officer*

GERALD J. MOSSINGHOFF

*Commissioner of Patents and Trademarks*